(12) United States Patent
Schwarz et al.

(10) Patent No.: US 10,842,782 B2
(45) Date of Patent: Nov. 24, 2020

(54) STORAGE STABLE COMPOSITION COMPRISING RIFAXIMIN ALPHA

(71) Applicant: Sandoz AG, Basel (CH)

(72) Inventors: Franz Xaver Schwarz, Kundl (AT); Arthur Pichler, Kundl (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 16/066,886

(22) PCT Filed: Mar. 22, 2017

(86) PCT No.: PCT/EP2017/056798
§ 371 (c)(1),
(2) Date: Jun. 28, 2018

(87) PCT Pub. No.: WO2017/162726
PCT Pub. Date: Sep. 28, 2017

(65) Prior Publication Data
US 2019/0008838 A1 Jan. 10, 2019

(30) Foreign Application Priority Data

Mar. 24, 2016 (EP) .................................... 16162417

(51) Int. Cl.
*A61K 31/437* (2006.01)
*A61K 9/20* (2006.01)
*A61K 9/28* (2006.01)

(52) U.S. Cl.
CPC .......... *A61K 31/437* (2013.01); *A61K 9/2054* (2013.01); *A61K 9/2095* (2013.01); *A61K 9/2866* (2013.01)

(58) Field of Classification Search
CPC .. A61K 31/437; A61K 9/2054; A61K 9/2095; A61K 9/2866; A61K 31/4188; C07B 2200/13
See application file for complete search history.

(56) References Cited

U.S. PATENT DOCUMENTS

| | | | |
|---|---|---|---|
| 3,283,885 A * | 11/1966 | Grunewald | A61J 1/035 116/308 |
| 9,018,225 B1 | 4/2015 | Hotha | |
| 2008/0262012 A1 | 10/2008 | Viscomi et al. | |
| 2010/0285164 A1 * | 11/2010 | Schaible | A61K 9/0056 424/777 |

FOREIGN PATENT DOCUMENTS

| | | | | |
|---|---|---|---|---|
| EP | 1557421 A1 | 7/2005 | | |
| EP | 1698630 A1 | 9/2006 | | |
| WO | WO-2005044823 A2 * | 5/2005 | ......... | C07D 498/22 |
| WO | WO-2006094737 A2 * | 9/2006 | ......... | A61K 9/0095 |
| WO | 2014091432 A1 | 6/2014 | | |

OTHER PUBLICATIONS

International Search Report and Written Opinion for PCT/EP2017/056798, dated May 24, 2017, 11 pages.
Preliminary Report from the International Preliminary Examining Authority for PCT/EP2017/056798, dated Mar. 22, 2017, 14 pages.
Handbook of Pharmaceutical Excipients, 3rd Edition, published by A.H. Kibbe. American Pharmaceutical Association, Washington, USA, and Pharmaceutical Press, London.
Lexikon der Hilfsstoffe für Pharmazie kosmetik und angrenzende Gebiete, published by H.P. Fielder, 4th Edition (in German).

* cited by examiner

*Primary Examiner* — Sarah Pihonak
(74) *Attorney, Agent, or Firm* — Luedeka Neely Group, P.C.

(57) ABSTRACT

The present invention relates to a pharmaceutical composition containing a stable polymorph of rifaximin and a wicking agent as well as a method of preparing the same.

10 Claims, 4 Drawing Sheets

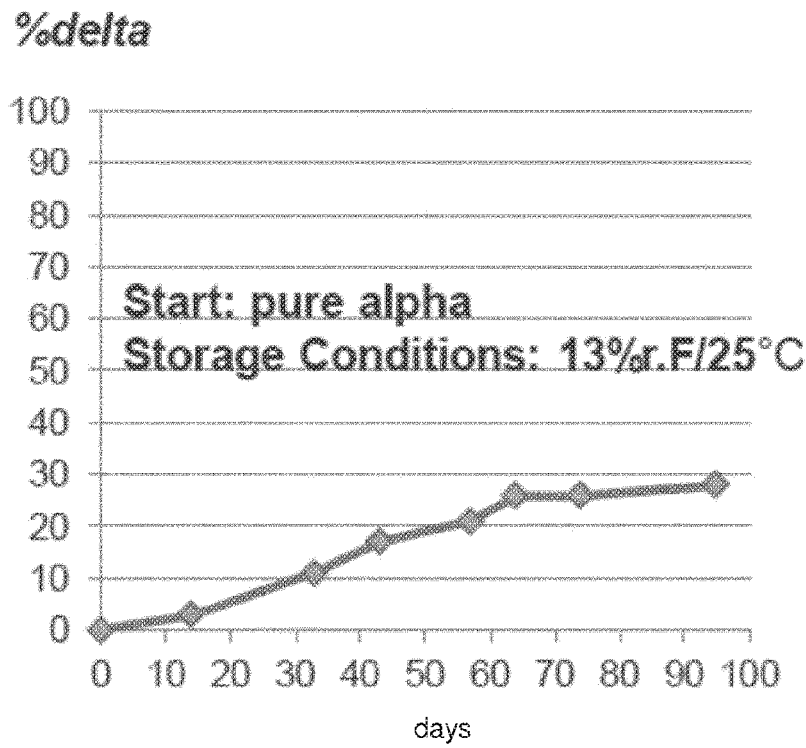
Figure 1: Amount of rifaximin delta formed in the comparative formulation (2.2) during storage at 13% RH and 25°C
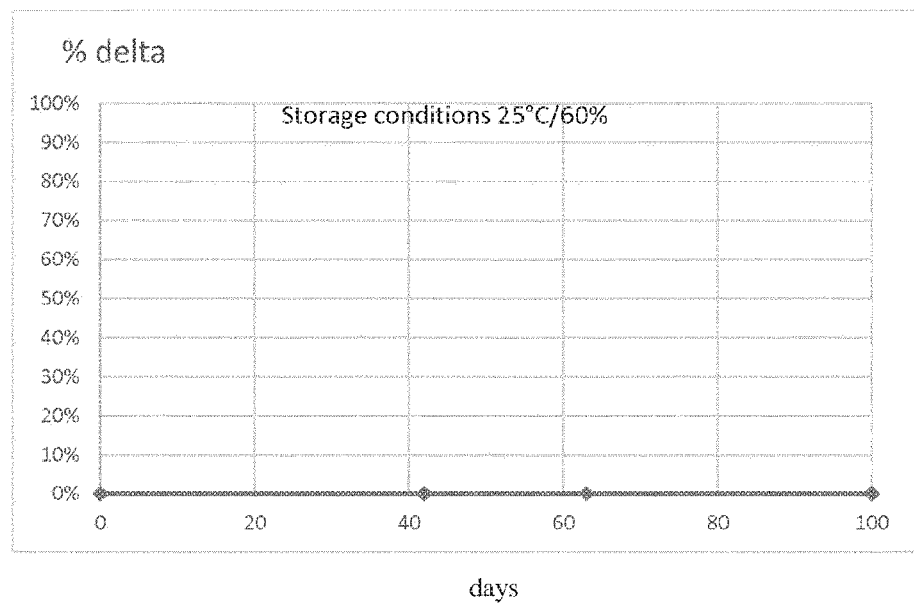
Figure 2: Amount of rifaximin delta formed in the composition of the present invention during storage at 60% RH and 25°C

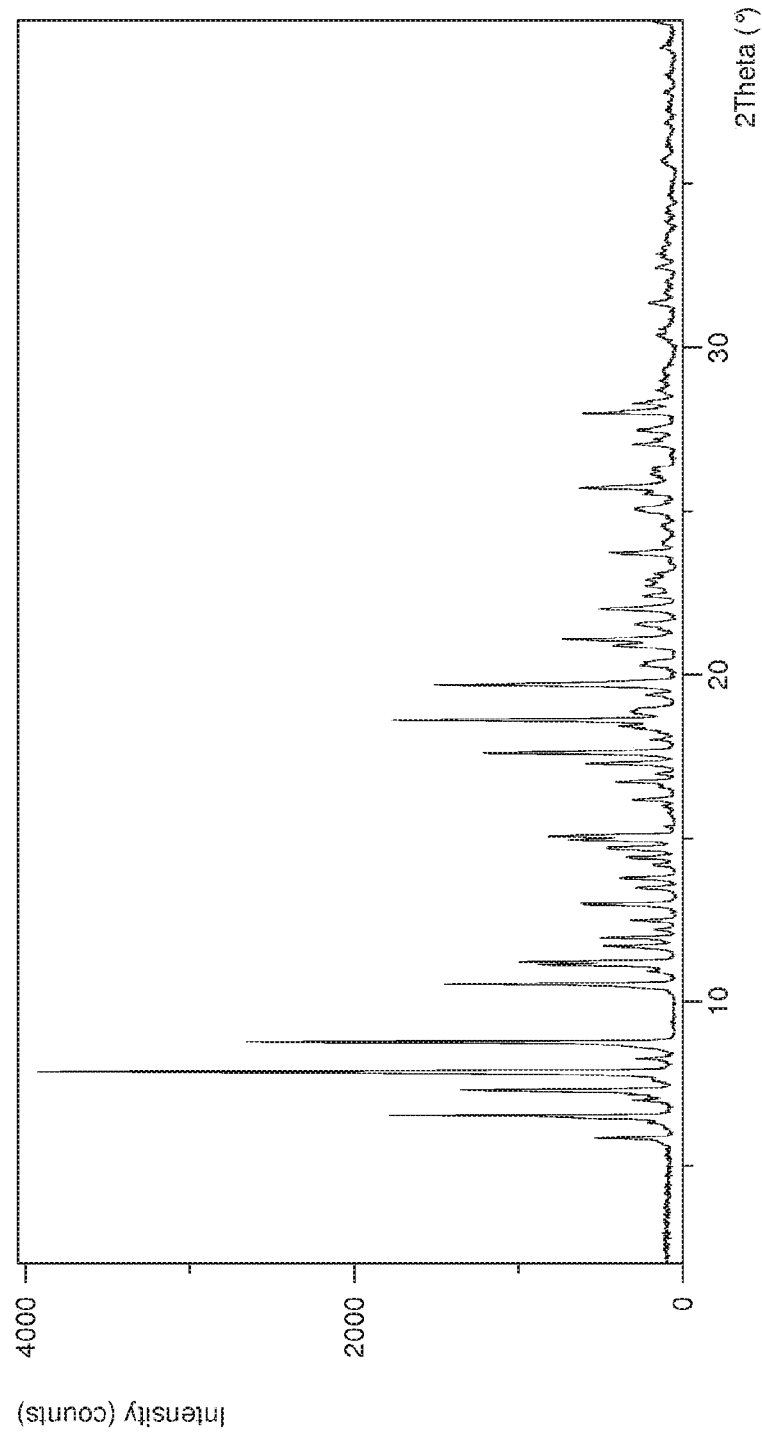
Figure 3: XRPD of form alpha

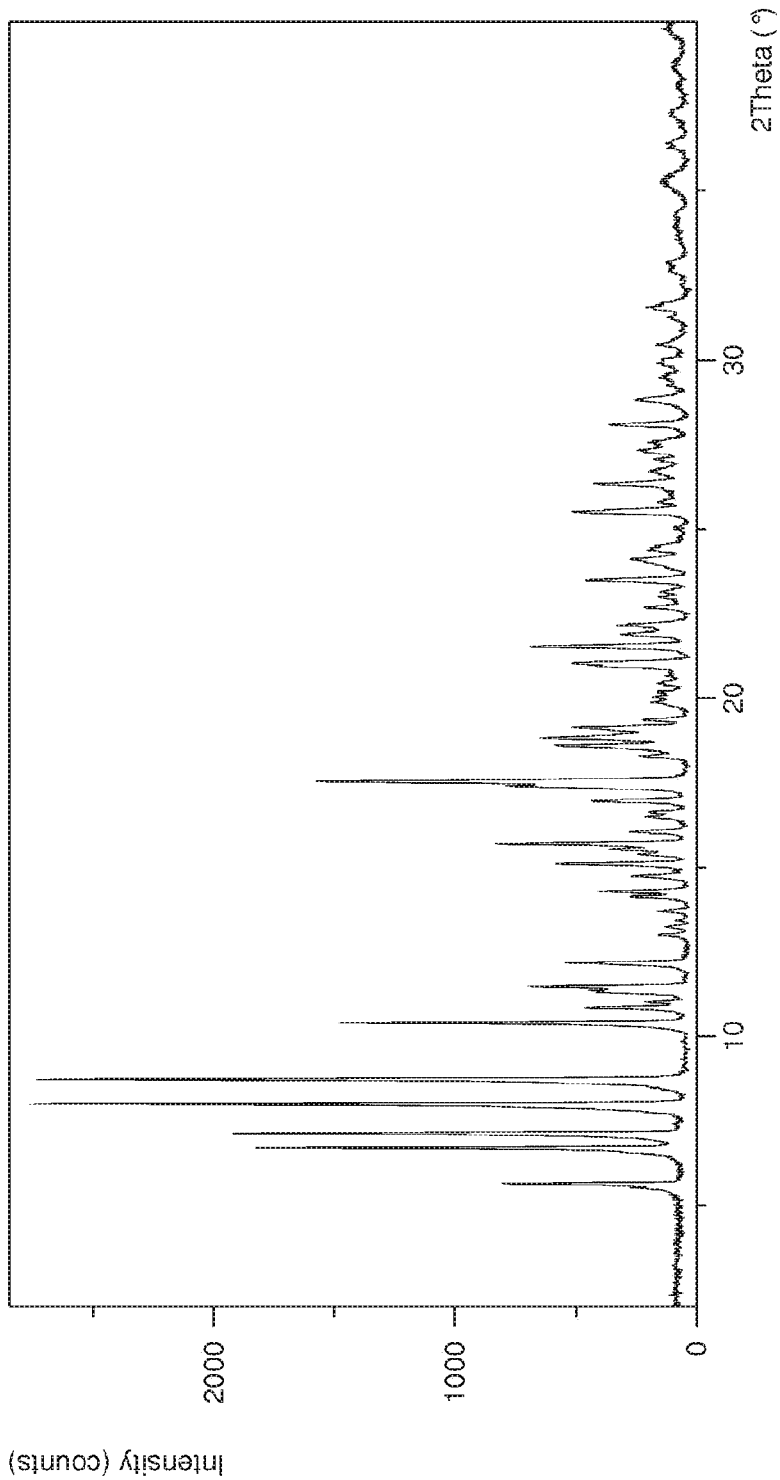
Figure 4: XRPD of form delta

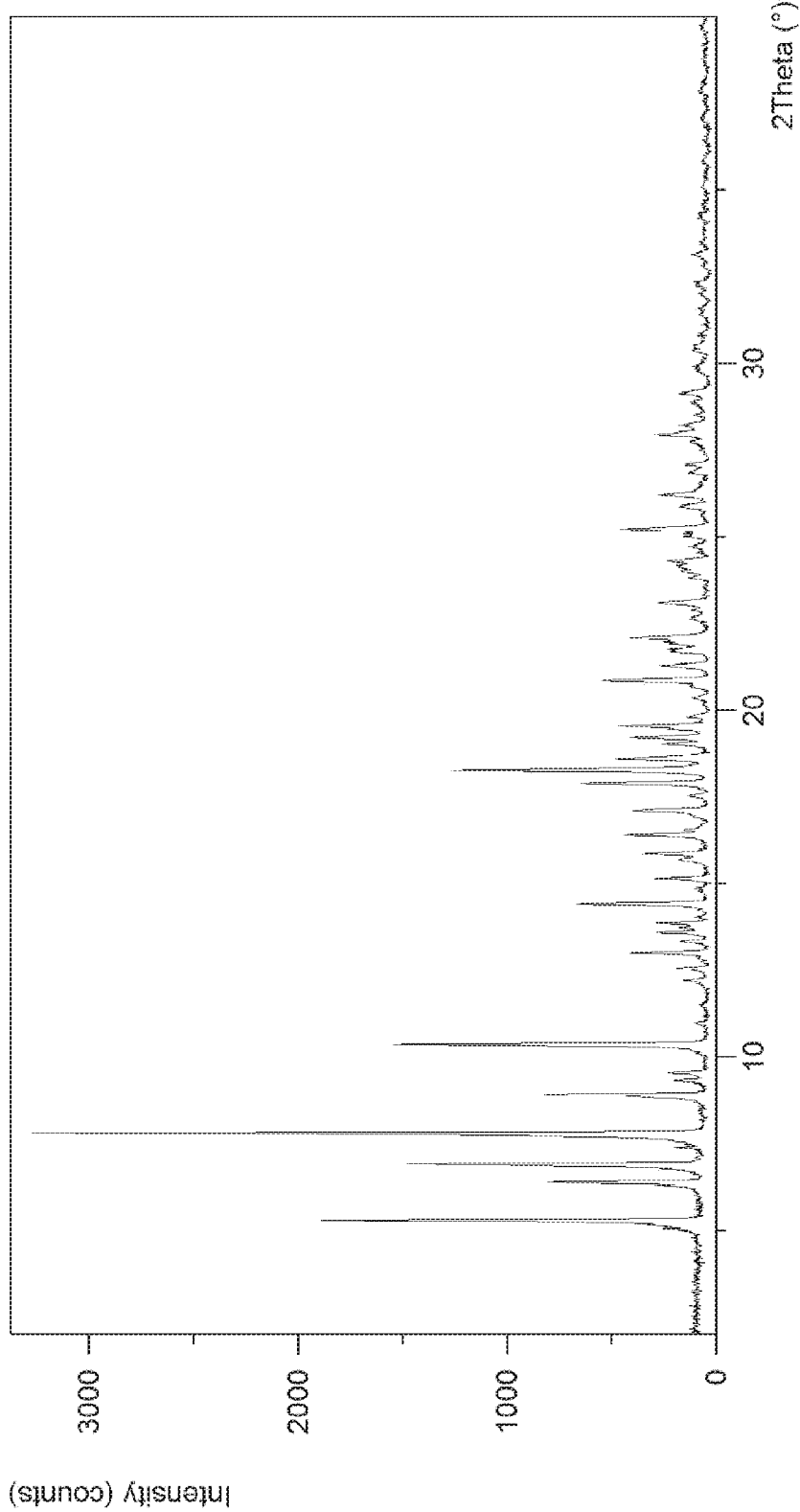
Figure 5: XRPD of form beta

STORAGE STABLE COMPOSITION COMPRISING RIFAXIMIN ALPHA

This application is a Section 371 national phase entry of PCT application PCT/EP2017/056798, filed Mar. 22, 2017. This application also claims the benefit of the earlier filing date of European patent application 16162417.6 filed Mar. 24, 2016.

The present invention relates to a pharmaceutical composition containing rifaximin alpha in a storage stable form and a wicking agent as well as a method of preparing the same.

BACKGROUND OF THE INVENTION

Rifaximin is a semisynthetic derivative of rifamycin, wherein rifaximin is an oral, bactericidal broad-spectrum antibiotic. The IUPAC name of rifaximin is (2S,16Z,18E,20S,21S,22R,23R,24R,25S,26S,27S,28E)-5,6,21,23,25-pentahydroxy-27-methoxy-2,4,11,16,20,22,24,26-octamethyl-2,7-(epoxypentadeca[1,11,13]trienimino) benzofuro[4,5-e]pyrido[1,2-a]-benzimidazole-1,15(2H)-dione,25-acetate and the compound is represented by the following formula

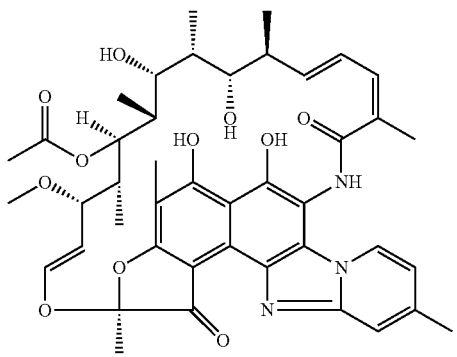 [SMILES: CO[C@H]1/C=C/O[C@@]2(C)Oc3c(C)c(O)c4c(O)c(c5c(nc6cc(C)ccn65)c4c3C2=O)NC(=O)/C(C)=C\C=C\[C@H](C)[C@H](O)[C@@H](C)[C@@H](O)[C@@H](C)[C@H](OC(C)=O)[C@@H]1C]

Rifaximin is reported to be poorly absorbed systemically, i.e. in the bloodstream, and as a consequence it shows its efficiency almost exclusively in the intestinal lumen.

Rifaximin can be used in the treatment of bacterial infections of the gastrointestinal tract, for example, in the treatment of traveler's diarrhea. Further, the active pharmaceutical agent can be used in the treatment or prevention of hepatic encephalopathy and is said to be efficacious in relieving chronic functional symptoms of bloating and flatulence that are common in irritable bowel syndrome (IBS).

Up to now more than 10 polymorphic forms of rifaximin have been described in the art. Many of these polymorphic forms can convert into each other. For example, EP 1 557 421 A1 describes the conversion of the β form into the α form and EP 1 698 630 discloses that under mild conditions the δ polymorph can convert to the ε polymorph. The different polymorphs are reported to possess different bioavailabilities.

Further, tablets containing rifaximin alpha are marketed under the tradename Xifaxan. However, when testing the storage stability of more than 10 different tablet batches from different countries, it turned out that after storage these tablets contain significant amounts of the δ polymorph. In other words, the tablets known in the art do not contain rifaximin alpha in a storage stable form, i.e. in a form which prevents the conversion into other polymorphic forms during shelf life.

The δ form is reported to have a higher systemic absorbance compared to the alpha form. After administration of a single 400 mg dose the following PK parameters have been found:

| Form | Cmax [ng/ml] | AUC [ng h/ml] |
| --- | --- | --- |
| Alpha | 2.6 | 17 |
| Delta | 308.3 | 830 |

Consequently, the conversion of one polymorphic form into another one is highly undesirable for the manufacturing of dosage forms containing rifaximin, especially in view of regulatory, efficacy and safety reasons.

Thus, there is a need for a pharmaceutical composition containing rifaximin, wherein a stable systemic absorbance of the drug during shelf life can be ensured. In particular, a constantly low systemic absorbance of the drug should be achieved after storage. Hence, it was an object of the present invention to overcome the drawbacks of the above-mentioned prior art.

In particular, it was an object of the present invention to provide a pharmaceutical composition containing rifaximin in form of one specific polymorph, wherein the polymorph does not convert into another polymorph of rifaximin. Thus, it was an object to provide a pharmaceutical composition in which one stabilized polymorphic form of rifaximin is present. Further, it was an object to provide a pharmaceutical composition containing rifaximin in a stabilized form which shows a poor systemic absorbance even after storage. In addition, a pharmaceutical composition with good workability should be provided.

According to the present invention, the above objects are unexpectedly achieved by a pharmaceutical composition comprising a specific polymorphic form of rifaximin and a wicking agent with a specific water content. Alternatively, the above objects are unexpectedly achieved by a pharmaceutical composition comprising a specific polymorphic form of rifaximin and a wicking agent, wherein the composition has a specific water activity.

Thus, a subject of the invention is a pharmaceutical composition, in particular a storage stable composition, comprising
(A) rifaximin in polymorphic form α
(B) wicking agent with a water content of less than 3 wt %, wherein the weight ratio of (A) rifaximin to (B) wicking agent is from 1:1 to 3:1. Preferably, the pharmaceutical composition is essentially free of other polymorphic forms of rifaximin.

An alternative subject of the invention is a pharmaceutical composition, in particular a storage stable composition, comprising
(A) rifaximin in polymorphic form α
(B) wicking agent
wherein the pharmaceutical composition has a water activity value of 0.005 to 0.09. Preferably, the weight ratio of (A) rifaximin to (B) wicking agent is from 1:1 to 3:1. Preferably, the pharmaceutical composition is essentially free of other polymorphic forms of rifaximin.

Both subjects are alternative solutions to the above-mentioned problem.

A further subject of the invention is the method for preparing a tablet according to the present invention comprising the steps of
(i) providing (A) rifaximin and (B) wicking agent (ii) optionally dry granulating the mixture of step (i) and optionally one or more further excipients
(iii) compressing the mixture from step (i) or the granulates from step (ii) and optionally further excipients to a tablet.

It was unexpectedly found that the pharmaceutical composition of the present invention allows stabilizing rifaximin in substantially one single polymorphic form, namely the polymorphic form α, during shelf life. Thus, by preventing the conversion into other polymorphic form(s) an advantageous composition can be provided which shows a reliable PK profile before and after storage.

BRIEF DESCRIPTION OF THE DRAWINGS

FIG. 1 is a graph illustrating the amount of rifaximin delta formed over time in a comparative rifaximin formulation;

FIG. 2 is a graph illustrating the amount of rifaximin delta formed over time in a rifaximin formulation in accordance with one embodiment of the present invention;

FIG. 3 is an X-Ray Powder Diffractogram (XRPD) showing characteristic peaks for rifaximin in polymorphic form α;

FIG. 4 is an X-Ray Powder Diffractogram (XRPD) showing characteristic peaks for rifaximin in polymorphic form δ; and FIG. 5 is an X-Ray Powder Diffractogram (XRPD) showing characteristic peaks for rifaximin in polymorphic form β.

DETAILED DESCRIPTION OF THE INVENTION

The present invention relates to a pharmaceutical composition comprising (A) rifaximin in polymorphic form α and (B) wicking agent with a water content of less than 3 wt %, wherein the weight ratio of (A) rifaximin to (B) wicking agent is from 1:1 to 3:1.

As indicated above, rifaximin can be present in different polymorphic forms. These polymorphic forms can be different crystalline forms and/or the result of stoichiometric and non-stoichiometric hydration or solvation.

A polymorphic form can be represented by one or more, preferably at least three, specific diffraction peaks in X-ray powder diffraction (XRPD).

In the present application, the XRPD is measured as described below in the experimental section.

Further, unless indicated otherwise, XRPD peaks are reported as degrees 2θ values with a standard error of ±0.2 degrees 2θ.

Compound (A) of the present application is rifaximin in polymorphic form α having diffraction peaks in the XRPD at 11.7, 13.0, and 19.6 degrees 2θ (±0.2 degrees 2θ). These peaks may be regarded as particularly characteristic diffraction peaks for rifaximin in polymorphic form α. Preferably, further peaks occur at 6.5, 7.3, 7.9, 8.7 10.5, 11.1, 17.6, 18.6, 21.1, 21.5 and/or 22.0 degrees 2θ (±0.2 degrees 2θ). A respective XRPD of form α is shown in FIG. 3.

Compound (A), rifaximin in polymorphic form α, preferably has a water content of 0.1 to 4.5 wt %, preferably of 0.5 to 3.0 wt %, more preferably of 1.0 to 2.5 wt %, in particular of about 1.5 to 2.0 wt %.

The composition of the present invention comprises rifaximin in form alpha, preferably pure form alpha. In other words, the composition does preferably not comprise other polymorphic forms of rifaximin.

In a preferred embodiment the composition is "essentially free" of rifaximin in polymorphic forms β and δ.

It is further preferred that the pharmaceutical composition of the present invention is "essentially" free of polymorphic form of rifaximin having a water content being higher than 5 wt %.

In another preferred embodiment, the pharmaceutical composition is "essentially free" of other polymorphic forms of rifaximin.

The term "essentially free" usually means that, apart from rifaximin in form α, the other polymorphic forms of rifaximin are present in such a low amount that they do not have a clinically significant influence on the bioavailability. Alternatively, the term "essentially free" usually means that the other polymorphic forms are present in such a low amount that they cannot be found in XRPD. In other words, in a preferred embodiment the drug of the pharmaceutical composition of the present invention only shows XRPD peaks which relate to form α. Consequently the drug, compound (A), can be regarded as pure rifaximin in polymorphic form α.

In a preferred embodiment the composition of the present invention, apart from rifaximin in polymorphic form α, comprises other polymorphic form(s) of rifaximin in an amount of less than 5 mol-%, more preferably less than 3 mol-%, based on the total molar amount of rifaximin. In particular the pharmaceutical composition of the present invention comprises less than 5 mol-%, more preferably less than 3 mol-% of rifaximin form delta.

The molar ratio of polymorphs, in particular the alpha/delta molar ratio, can preferably be determined by the "Rietveld Analysis" of powder X-ray diffraction data, wherein the diffraction data are obtained as described below in the experimental section.

Rifaximin in polymorphic form δ is represented as having diffraction peaks in the XRPD at 5.6, 12.2 and 17.0 degrees 2θ (±0.2 degrees 2θ). Further peaks can occur at 6.7, 7.1, 8.0, 8.7 10.4, 10.8, 11.3, 17.4, 17.5, 18.6, 18.8, 19.1, 21.0 and/or 21.5 degrees 2θ (±0.2 degrees 2θ). A respective XRPD of form δ is shown in FIG. 4.

Rifaximin in polymorphic form β is represented as having diffraction peaks in the XRPD at 5.3, 10.4 and 18.3 degrees 2θ (±0.2 degrees 2θ). Further peaks can occur at 6.4, 6.9, 7.8, 8.9, 9.3, 9.5, 12.2, 12.6, 13.0, 13.6, 13.9, 14.4, 15.1, 15.8, 16.4, 17.1, 17.9, 18.6, 19.0, 19.2, 19.5, 20.8, 21.3, 21.7, 22.1, 23.1, 24.3, 25.2, 26.2 and/or 27.9 degrees 2θ (±0.2 degrees 2θ). A respective XRPD of form β is shown in FIG. 5.

In an especially preferred embodiment the present composition contains rifaximin in polymorphic form α in an amount of more than 98.5%, preferably more than 99%, in particular more than 99.5%, based on the amount of rifaximin.

In a preferred embodiment the composition of the present invention is essentially free of other polymorphic forms of rifaximin, even after storing it for 6 months. Hence, the composition of the present invention is referred to as "storage stable".

Compound (B) of the composition according to the invention is a wicking agent, preferably a wicking agent having a specific water content.

Generally, a wicking agent can be regarded as a material with the ability to draw a liquid, preferably water, into the network of the material. Wicking agents can be characterized by having the ability to undergo physisorption with a liquid, preferably water. Physisorption is defined as a form of adsorption in which the molecules of the liquid can loosely adhere to surfaces of the wicking agent via van der Waals' interaction between the surface of the wicking agent and the adsorbed molecule. In the case of a pharmaceutical composition, the adsorbed molecule is primarily water or another biological fluid which is mainly composed of water. A wicking agent can do this with or without swelling. Some materials can both wick water and swell, others can function as wicking agents only.

Wicking agent (B) included in the pharmaceutical composition or the corresponding dosage form according to the present invention has or creates channels or pores in said pharmaceutical composition or the corresponding dosage form. This preferably facilitates the channeling of water molecules through the pharmaceutical composition or corresponding dosage form by physisorption. The function of the wicking agent is to carry water to surfaces inside its core, thereby creating channels or a network of increased surface area.

Materials suitable for acting as wicking agents include, but are not limited to, microcrystalline cellulose, silicified microcrystalline cellulose, lactose, colloidal silicon dioxide, kaolin, titanium dioxide, fumed silicon dioxide, alumina, niacinamide, sodium lauryl sulfate, low molecular weight polyvinyl pyrrolidone, m-pyrol, bentonite, magnesium aluminum silicate, polyester, polyethylene and mixtures thereof.

In a preferred embodiment of the present invention wicking agent (B) is selected from microcrystalline cellulose, silicified cellulose, lactose and mixtures thereof. In a particularly preferred embodiment wicking agent (B) is microcrystalline cellulose.

In the present invention wicking agent (B) has a water content of less than 3 wt %. It is preferred that the wicking agent has a water content of less than 2.5 wt %, more preferably less than 2.0 wt %. In a particularly preferred embodiment wicking agent (B) has a water content of less than 1.5 wt %. The lower limit of the water content could be e.g. 0.01 wt %, 0.1 wt %, 0.2 wt % or 0.5 wt %.

The water content can preferably be determined as described below in the experimental section.

It turned out that the use of a wicking agent having the before-mentioned water content ensures the stabilization of rifaximin in form of one specific polymorph, in particular rifaximin in polymorphic form α, as well as the good workability (e.g. compressability, flowability) of the pharmaceutical composition.

Alternatively preferred, the pharmaceutical composition has a water activity value from 0.005 to 0.09, preferably from 0.01 to 0.8, in particular from 0.02 to 0.07. Contrary to the content of water of a substance/composition, the activity of water is a measure for the "active" or "available" water of the substance/composition. The activity of water value ($a_w$) is defined as the ratio of the water vapor partial pressure of the substance (p) to the saturated vapor pressure of pure water ($p_0$) at a distinct temperature and thus can be calculated from the following equation:

$$a_w = p/p_0$$

The water activity value of a substance/composition can preferably be determined as described below in the experimental section.

It is further preferred hat the wicking agent (B) has a water activity value being smaller than the one of rifaximin (A). The water activity value of rifaximin (A) can be from 0.001 to 0.1, preferably from 0.005 to 0.08, more preferably from 0.01 to 0.06. Further, the water activity value of wicking agent (B) can preferably be from 0.005 to 0.07, more preferably from 0.01 to 0.06.

In a preferred embodiment the above described embodiment could be combined. This means that a further subject of the present invention is a pharmaceutical composition comprising
(A) rifaximin in polymorphic form α
(B) wicking agent having a water content of less than 3 wt.-%,
wherein preferably the weight ratio of (A) rifaximin to (B) wicking agent is from 1:1 to 3:1, and wherein the pharmaceutical composition has a water activity value from 0.005 to 0.09. Further, the pharmaceutical composition is essentially free of other polymorphic forms of rifaximin.

The pharmaceutical composition of the present invention comprises rifaximin (A) and wicking agent (B) in a weight ratio of 1:1 to 3:1, preferably 1.05:1 to 2.5:1, more preferably 1.1:1 to 2.25:1, even more preferably 1.15:1 to 2:1, in particular, 1.2:1 to 1.8:1.

It is further preferred that wicking agent (B) has an average particle size between 20 μm and 200 μm, preferably between 30 μm and 175 μm, in particular between 40 μm and 150 μm. The term "average particle size" refers to the volume average particle size ($D_{50}$), which can be determined by the light scattering method using a Mastersizer 2000 apparatus made by Malvern Instruments (wet measurement, paraffin as dispersant, 2000 rpm, ultrasonic waves for 60 sec., data interpretation via Fraunhofer method).

In a preferred embodiment wicking agent (B) has a bulk density between 0.23 and 0.37 g/cm$^3$, preferably between 0.24 and 0.36 g/cm$^3$, particularly between 0.25 and 0.35 g/cm$^3$.

The bulk density is a property of a substance preferably present in powder form or as granules. It is defined as the mass of many particles of the material divided by the total volume they occupy. The total volume includes particle volume, inter-particle void volume and internal pore volume. The bulk density does not need to be an intrinsic property of a material; it can change depending on how the material is handled.

The bulk density can be calculated by the following equation:

$$\rho = M/V,$$

wherein
M is the mass of the corresponding substance measured in g and
V is the volume of the corresponding substance measured in cm$^3$.

The bulk density can be determined according to Ph. Eur. 6.0, 2.9.15.

It is further preferred that the pharmaceutical composition of the present invention further comprises one or more pharmaceutically acceptable excipients.

Suitable pharmaceutical excipients are for example disclosed in "Lexikon der Hilfsstoffe für Pharmazie, Kosmetik und angrenzende Gebiete", published by H. P. Fielder, 4$^{th}$ Edition, and "Handbook of Pharmaceutical Excipients", 3$^{rd}$ Edition, published by A. H. Kibbe, American Pharmaceutical Association, Washington, USA, and Pharmaceutical Press, London.

Pharmaceutically acceptable excipient(s) can for example be disintegrants, glidants and lubricants.

Disintegrants are compounds which enhance the ability of the dosage form, preferably the ability of the tablet, to break into smaller fragments when in contact with a liquid, preferably water. Suitable disintegrants are for example croscarmellose sodium, sodium carboxymethyl starch, cross-linked polyvinylpyrrolidone (crospovidone), sodium carboxymethylglycolate (=sodium starch glycolate) and sodium bicarbonate, preferably cross-linked polyvinylpyrrolidone (crospovidone) and sodium carboxymethylglycolate. The disintegrant can be present in an amount of 0 to 20% by weight, preferably in an amount of 1 to 15% by weight, based on the total weight of the pharmaceutical composition.

Glidants can be used to improve the flowability. Suitable glidants are for example colloidal silicon dioxide, talcum or mixtures thereof. The glidant can be present in an amount of 0 to 8% by weight, preferably in an amount of 0.1 to 3% by weight, based on the total weight of the composition.

Lubricants generally can be regarded as substances which are suitable to reduce friction, such as static friction, sliding friction and rolling friction. In particular, lubricants reduce the shearing forces occurring on the borderline between tablet and mould, especially the sliding friction found during tablet pressing between the punch moving up and down in the die and the die wall on the one hand and between the edge of the tablet and the die wall on the other hand. Lubricants can be for example alkaline earth metal salts of fatty acids, such as magnesium stearate. Alternatively, lubricants can be esters, preferably diesters of glycerol with fatty acids, such as glycerol stearate palmitate. The lubricant can be present for example in an amount of 0 to 5% by weight, preferably in an amount of 0.5 to 2.5% by weight based on the total weight of the composition.

In a preferred embodiment the composition of the present invention comprises:
- 45-75 wt % rifaximin (A), preferably 50-65 wt % rifaximin (A), in particular 54-60 wt % rifaximin (A)
- 10-45 wt % wicking agent (B), preferably 20-40 wt % wicking agent (B), in particular 25-35 wt % wicking agent (B), e.g. microcrystalline cellulose
- 0-10 wt % disintegrant, preferably 1.5-8 wt % disintegrant, in particular 2.5-6 wt % disintegrant, e.g. sodium starch glycolate
- 0-5 wt % glidant, preferably 0.5-4.5 wt % glidant, in particular 1-3 wt % glidant, e.g. talc and/or colloidal silicon dioxide,
- 0-5 wt % lubricant, preferably 0.3-4 wt % lubricant, in particular 0.6-2 wt % lubricant, e.g. glycerol stearate palmitate, wherein the wt % are based on the total weight of the composition.

The pharmaceutical composition can be preferably present in an oral dosage form, such as a capsule or tablet, preferably a tablet. In other words, another subject of the present invention is an oral dosage form, comprising the composition of the present invention as described above and below.

In case that the oral dosage form is a tablet, the tablet can preferably be coated or uncoated, preferably coated, more preferably film-coated.

Generally, film coatings that do not affect the release of the active agent(s) and film coatings affecting the release of the active agent(s) can be employed with tablets according to invention. The film coatings that do not affect the release of the active agent(s) are preferred.

Preferred examples of film coatings which do not affect the release of the active ingredient can be those including poly(meth)acrylate, methylcellulose (MC), hydroxypropyl methylcellulose (HPMC), hydroxypropyl cellulose (HPC), hydroxyethyl cellulose (HEC), polyvinylpyrrolidone (PVP), polyvinylalcohol (PVA) and mixtures thereof. More preferred is hydroxypropyl methylcellulose (HPMC). These polymers can have a weight-average molecular weight of 10,000 to 150,000 g/mol.

In a preferred embodiment the film can have a thickness of 2 µm to 150 µm, preferably 10 to 100 µm, more preferably 20 to 60 µm.

The preferred coating may comprise a film-forming agent and one or more of the following: lubricant, surfactant, glidant, pigment and water.

In a preferred embodiment of the present invention the dosage form of the present invention is packed by a suitable packaging material. The packaging material preferably reduces or prevents water exchange between the pharmaceutical composition of the present invention and the environment. For example, if the dosage forms are tablets or capsules, suitable blister pack materials can be used. The blister pack may comprise a cavity or pocket, preferably containing a thermoformed plastic. This usually has as a backing a lidding seal containing an aluminum and/or plastic foil. Further, if the composition is in form of a granulate, suitable sachets can be used.

In a particularly preferred embodiment the pharmaceutical composition or the dosage form of the present invention is packed by a material having a water vapor permeability of 0.001 to 0.15 g/m$^2$/day at 38° C./5%/90% RH, preferably of 0.01 to 0.12 g/m$^2$/day at 38° C./5%/90% RH, in particular 0.05 to 0.10 g/m$^2$/day at 38° C./5%/90% RH, wherein said water vapor permeability is determined according to ASTM F1249-13. Preferably, a Permatran-W Model 3/33 device is used. The measurement is preferably carried out at 38° C. Further, preferably the humidity in the dry chamber is 5% relative humidity (=RH), whereas the humidity in the wet chamber is 90% RH.

In a preferred embodiment the packaging material can preferably be selected from polyvinylchloride (PVC), polyvinylidenchloride (PVDC), polyethylene (PE), polypropylene (PP), polyethylenterephthalate (PET) polystyrol (PS), polyamide and alumina or combinations thereof.

In a preferred embodiment the packing material comprises layered sheets, which can be thermoformed, containing one or more layers. In a preferred embodiment the packing material can be a composite material, e.g. co-extruded composite material, e.g. a polyamide-alumina-polyvinyl chloride composite material, which is also referred to as Nylon®-Alu-PVC.

In a preferred embodiment the packaging material has a thickness of 1 µm to 1 mm. In case of a blister pack the thermoformed plastic pocket preferably has a thickness of 100 to 1000 µm, more preferably of 150 to 800 µm. Further, the backing foil usually has a thickness of 10 to 150 µm, more preferably of 15 to 100 µm.

A further subject of the present invention is a method for preparing a tablet according to the invention comprising the steps of
(i) providing (A) rifaximin and (B) wicking agent.
(ii) optionally dry granulating the mixture of step (i) and one or more further excipients,
(iii) compressing the mixture from step (i) or the granules from step (ii) and optionally further excipient(s) to a tablet, and
(iv) optionally film coating the tablet and
(v) optionally packaging the tablet.

As far as (A) rifaximin. (B) wicking agent and excipients are concerned, for the present method the same applies as to the before-mentioned pharmaceutical composition.

In step (i) rifaximin (A) and wicking agent (B) are provided. Preferably, the wicking agent having the water content as described above is used. It is preferred that rifaximin (A) and wicking agent (B) and optionally one or more further excipient(s) can be blended in order to provide a composition having a homogenous distribution of rifaximin (A) and wicking agent (B) within the resulting blend comprising rifaximin (A) and wicking agent (B). Blending can be carried out with conventional mixing devices, e.g. in a free-fall mixer. Blending can be carried out e.g. for 1 minute to 30 minutes, preferably for 2 minutes to less than 10 minutes.

It is further preferred that the blend of rifaximin (A) and wicking agent (B) and optionally one or more further excipient(s) can be sieved, preferably with a sieve having a mesh size of 25 to 1000 μm, preferably 50 to 800 μm, especially 100 to 600 μm.

In optional step (ii) the mixture from step (i) and optionally one or more further excipient(s) can be dry-granulated.

"Dry" is usually understood to mean that the step is carried out in the absence of a liquid, in particular in the absence of water. "Granulating" is generally understood to mean the formation of relatively coarse or granular aggregate material as a powder by assembling and/or aggregating finer powder particles (agglomerate formation or build-up granulation) and/or the formation of finer granules by breaking up coarser aggregates (disintegration or break-down granulation). Dry granulation can preferably be carried out by using pressure or temperature. In a preferred embodiment of the invention, granulating the mixture from step (i) can be performed for example by "slugging", using a large heavy-duty rotary press and breaking up the slugs into granulates with a hammer mill or by roller compaction, using for example roller compactors by Powtec or Alexanderwerk. The granulates are then optionally screened.

In step (iii) the mixture of step (i) or the granules of step (ii) and optionally further excipient(s) can be compressed into a tablet. Compressing the mixture of step (i) or the granulates from step (ii) into a tablet can preferably be carried out by compressing said formulation on a rotary press. The main compression force can range from 1 to 50 kN, preferably from 3 to 40 kN. The resulting tablets can have a hardness of 30 to 400 N, more preferably of 50 to 250 N, particularly preferably of 30 to 180 N, more preferably of 40 to 150 N, wherein the hardness can be measured according to Ph. Eur. 6.0. Chapter 2.9.8.

In a preferred embodiment steps (i), (ii) and (iii) can be performed under non-humid conditions. In particular, these steps can be performed at a temperature of from 0° C. to 30° C., preferably 10° C. to 25° C. Further, said process is preferably performed at 0 to 40% RH or less, preferably at 5 to 20% RH. The same conditions can be chosen for optional steps (iv) and (v).

Further, the dosage form, preferably the tablet, of the invention preferably has a content uniformity, i.e. a content of active agent(s) which lies within the concentration of 90 to 110%, preferably 95 to 105%, especially preferred of 98 to 102% of the average content of the active agent(s). The "content uniformity" is determined with a test in accordance with Ph. Eur., 6.0, Chapter 2.9.6. According to that test, the content of the active agent of each individual tablet out of 20 tablets must lie between 90 and 10%, preferably between 95 and 105%, especially between 98 and 102% of the average content of the active agent(s). Therefore, the content of the active agent in each tablet of the invention differs from the average content of the active agent by at most 10%, preferably at most 5% and especially at most 2%.

In addition, the resulting tablet preferably has a friability of less than 5%, particularly preferably less than 2%, especially less than 1%. The friability is determined in accordance with Ph. Eur., 6.0, Chapter 2.9.7. The friability of tablets generally refers to tablets without coating.

In a optional step (iv) the tablets from step (iii) can preferably be film coated, wherein film coatings such as Opadry II can be used.

In a further optional step (v) the tablets from step (iii) or (iv) can be packaged. Preferably, the materials as described above are used.

The invention shall be illustrated by the following examples.

EXAMPLES

1. Analytical Methods 1.1 XPRD & Rietveld Refinement

Parameters XRPD: X-ray powder diffraction patterns (XRPD) were obtained with an X'Pert PRO diffractometer (PANalytical, Almelo, Netherlands) equipped with a theta/theta coupled goniometer in transmission geometry, programmable XYZ-stage with well plate holder. Cu-K$\alpha$1,2 radiation source (wavelength 0.15419 nm) with a focusing mirror, a 0.5° divergence slit, a 0.04 rad Soller slit collimator and a 0.5° anti-scattering slit on the incident beam side, a 1.4 mm anti-scattering slit, a 0.02 rad Soller slit collimator, a Ni-filter and a 1d-PIXcel solid state line detector (255 channels) on the diffracted beam side. The patterns were recorded at a tube voltage of 45 kV, tube current of 40 mA, applying a stepsize of 0.013° 2-theta with an exposure time of 40 s per step in the angular range of 2° to 40° 2-Theta at ambient conditions, preferably at 25° C. and 20% RH. A typical precision of the 2-Theta values is in the range of about ±0.2° 2-Theta. Thus a diffraction peak that appears at 6.6° 2-Theta can appear between 6.4 and 6.8° 2-Theta on most X-ray diffractometers under standard conditions.

Rietveld refinement of the sample's phase composition was done by Highscore 4.1 from Panalytical. Crystal structures were received from the Cambridge structural database as described in Braga et al., CrystEngComm, 2012, 14, 6404-6411. Atom positions are taken directly from single-crystal structure and are not refined; no correction is attempted for the fact that the single-crystal structures are measured at 25° C. An overall isotropic Debye-Waller factor was refined with the same value for all phases. Refined parameters are the zero point, scaling factors, lattice parameters, 5 background points, 3 peak-width parameters and 1 parameter of anisotropic broadening. Preferred orientation correction in hkl 1 1 0 is refined for the main phases with the 1-parameter March model.

1.2 Water Content According to Karl Fischer

The water content was determined according to Ph. Eur 6.0, 2.5.12 Method A, wherein an Excellence Titrator T70 (Mettler Toledo) was used.

Preferably, the following measurement parameters can be used:

Weight sample: 200 mg
Density: 1.0 g/mL
Temperature: 25° C.
Titration agent: KF1-comp 5
Nominal concentration: 5 mg/mL
Weight 0.015 g
Temperature: 25° C.
Duration for mixing: 30 sec
Sensor type: polarised
Sensor DM 143-SC
Unit: mV
Indication voltametric Ipol 24.0 μA
Stirring: 35%
Regulation:
Endpoint: 100.0 mV
Control band: 400.0 mV
Dosing rate (max): 5 mL/min
Dosing rate (min): 80 μL/min
Stop
Type: Driftstop absolut
Drift 25 μg/min
at Vmax: 50 mL
Time (min) 0
Time (max.) ∞
Calculation
Result: Content
Result (unit) %
Formula: R1=(VEQ·CONC·TIME·DRIFT/1000)·C/m
Constant C=0.1

The sample is prepared and weighted in a glove box with less than 5% RH. For determination of the water content 5 samples were measured and the average from the corresponding values was calculated.

1.3 Water Activity

Determination of the relative humidity (in %) in the air above a specimen after establishment of the humidity equilibrium in a closed system at constant temperature with the following equipment:

Hygrometer chamber Rotronic AW-VC and hygrometer BT-RS1

Temperature: 25±1° C.

Glove box: flushed with dry air or nitrogen, equipped with hygrometer, 5% RH

Procedure:

The sample dish was filled with the specimen and the sample dish was placed in the measuring chamber, which had been thermostated to 25±1° C. Then, the measuring chamber was sealed. When equilibrium of the relative humidity was established (trend indication disappears), the corresponding value was determined.

2. Preparation of Tablets 2.1 Tablets According to the Invention

Rifaximin in polymorphic form α, microcrystalline cellulose having a water content of not more than 1.5 wt. %, colloidal silicon dioxide and sodium starch glycolate were mixed together for 15 minutes at 23 rpm in a "Heidolph Reax 2 Überkopfmischer". The mixture is dry granulated. Talc and glycerol palmitostearate were added to the granules and the mixture was blended. The final blend was compressed on a press and the resulting tablets were film coated with Opadry II 85F540027 such that the resulting tablets each contained

| Rifaximin | 550 mg |
| Microcrystalline cellulose | 315 mg |
| Colloidal silicon dioxide | 12.5 mg |
| Sodium starch glycolate | 38.5 mg |
| Talc | 10.5 mg |
| Glycerol palmitostearate | 13.5 mg |
| Opadry II 85F540027 film coating | 23 mg |

2.2 Comparative Formulation

Rifaximin in polymorphic form α, microcrystalline cellulose having a water content of 5 wt. %, colloidal silicon dioxide and sodium starch glycolate were mixed together for 15 minutes at 23 rpm in a "Heidolph Reax 2 Überkopfmischer". The mixture was dry granulated. Talc and glycerol palmitostearate were added to the granules and the mixture was blended. The final blend was compressed on a press and the resulting tablets were film coated with Opadry II 85F540027 such that the resulting tablets each contained

| Rifaximin | 550 mg |
| Microcrystalline cellulose | 315 mg |
| Colloidal silicon dioxide | 12.5 mg |
| Sodium starch glycolate | 38.5 mg |
| Talc | 10.5 mg |
| Glycerol palmitostearate | 13.5 mg |
| Opadry II 85F540027 | 23 mg |

3. Storage Test

As can been seen from FIG. 1, even being stored under relatively mild conditions, significant amounts of rifaximin δ were formed in the comparative formulation. In other words, rifaximin form α was not present in a stabilized form.

Contrary. FIG. 2 shows the storage behaviour of the composition of the present invention. Though the relative humidity is even higher than the one used for the storage conditions with regard to the comparative formulation, it is demonstrated that there is no recognizable conversion from form alpha into form delta, i.e. rifaximin alpha is present in an unexpectedly stable form.

The invention claimed is:

1. Pharmaceutical composition comprising
   (A) rifaximin in polymorphic form α and
   (B) wicking agent with a water content of less than 3 wt %,
wherein the weight ratio of (A) rifaximin to (B) wicking agent is from 1:1 to 3:1, and wherein the pharmaceutical composition is essentially free of other polymorphic forms of rifaximin, and
   wherein the pharmaceutical composition is present as a tablet.

2. Pharmaceutical composition comprising
   (A) rifaximin in polymorphic form α and
   (B) wicking agent,
wherein the pharmaceutical composition has a water activity value from 0.005 to 0.09, and wherein the pharmaceutical composition is essentially free of other polymorphic forms of rifaximin, and
   wherein the pharmaceutical composition is present as a tablet.

3. Pharmaceutical composition according to claim 1, wherein the wicking agent is selected from microcrystalline cellulose, silicified cellulose, lactose and mixtures thereof.

4. Pharmaceutical composition according to claim 3, wherein the wicking agent is microcrystalline cellulose.

5. Pharmaceutical composition according to claim 1, wherein the wicking agent has an average particle size (D50) of 20 μm to 200 μm.

6. Pharmaceutical composition according to claim 1, wherein the wicking agent has a bulk density between 0.23 and 0.37 g/cm$^3$.

7. Pharmaceutical composition according to claim 1 comprising
   45-75 wt % of the rifaximin (A) in polymorphic form α,
   10-45 wt % of the wicking agent (B) with a water content of less than 3 wt %,
   optionally 1-10 wt % disintegrant,
   optionally 0.5-5 wt % glidant, and
   optionally 0.1-5 wt % lubricant.

8. Oral dosage form according to claim 1, wherein the dosage form is packed by a packaging material.

9. Method for preparing a dosage form according to claim 1 comprising the steps of (i) providing (A) rifaximin in polymorphic form α and (B) wicking agent with a water content of less than 3 wt %
(ii) optionally dry granulating the mixture from step (i) and optionally one or more further excipients
(iii) compressing the mixture from step (i) or the granulates from step (ii) and optionally further excipient(s) to a tablet,
wherein the weight ratio of (A) rifaximin to (B) wicking agent in the tablet is from 1:1 to 3:1, and wherein the tablet is essentially free of other polymorphic forms of rifaximin.

10. Method according to claim 9, wherein step (ii) comprises compacting the mixture of step (i) to a slug and further granulating the slug.

\* \* \* \* \*